United States Patent [19]
Piron

[11] Patent Number: 6,153,066
[45] Date of Patent: Nov. 28, 2000

[54] TOOL HOLDING DEVICE FOR THE EXTRACTION AND TRANSFER OF ANODES IN THE CENTER OF AN ALUMINUM FACTORY AND EQUIPMENT FOR OPERATING SUCH

[76] Inventor: Gérard Piron, 1 Quai de Serbie, 69006 Lyons, France

[21] Appl. No.: 09/250,633

[22] Filed: Feb. 16, 1999

[51] Int. Cl.[7] ................................................... C25C 3/00
[52] U.S. Cl. ............................................................ 204/245
[58] Field of Search ............................. 204/245; 205/389

[56] References Cited

U.S. PATENT DOCUMENTS 5,435,897  7/1995  Zannini ................................. 204/245

*Primary Examiner*—Kathryn Gorgos
*Assistant Examiner*—Thomas H Parsons

[57] ABSTRACT

The invention relates to a tool holder module intended to be used in lifting gear, characterized in that it is equipped with two independently motorized lifting member:

- a first member, which consists of a lifting system with cable(s) wrapped over electrically motorized drum(s) and returned at a sheaving system, said first member being intended to displace a load at a relatively high speed and over a relatively large distance;
- a second member, one of the constituent elements of which is secured to the end of the cable or cables of said first member after return at the sheaving system and is intended, in cooperation with this system, to displace a heavier load vertically at a lower speed and over a limited distance.

15 Claims, 6 Drawing Sheets

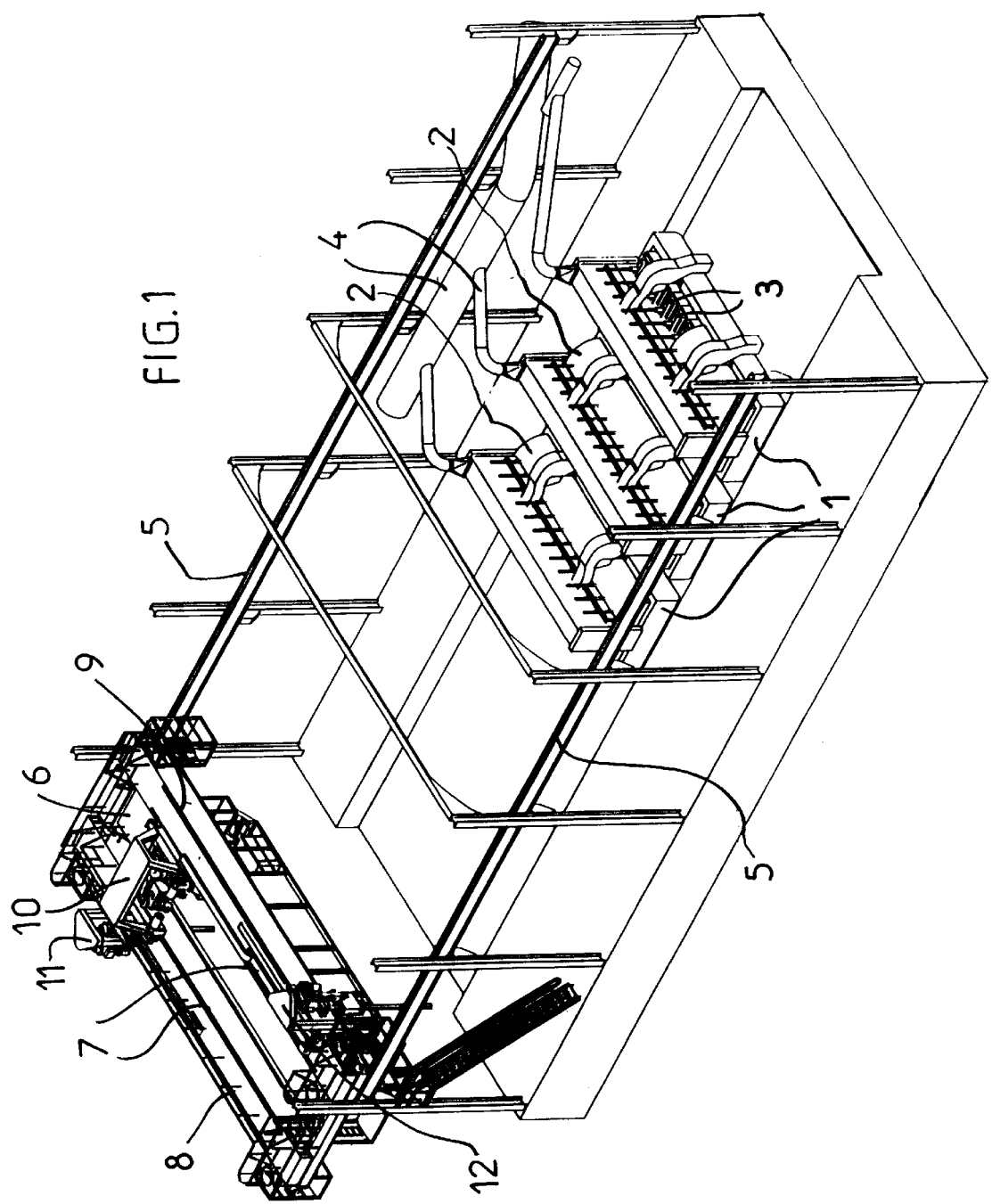

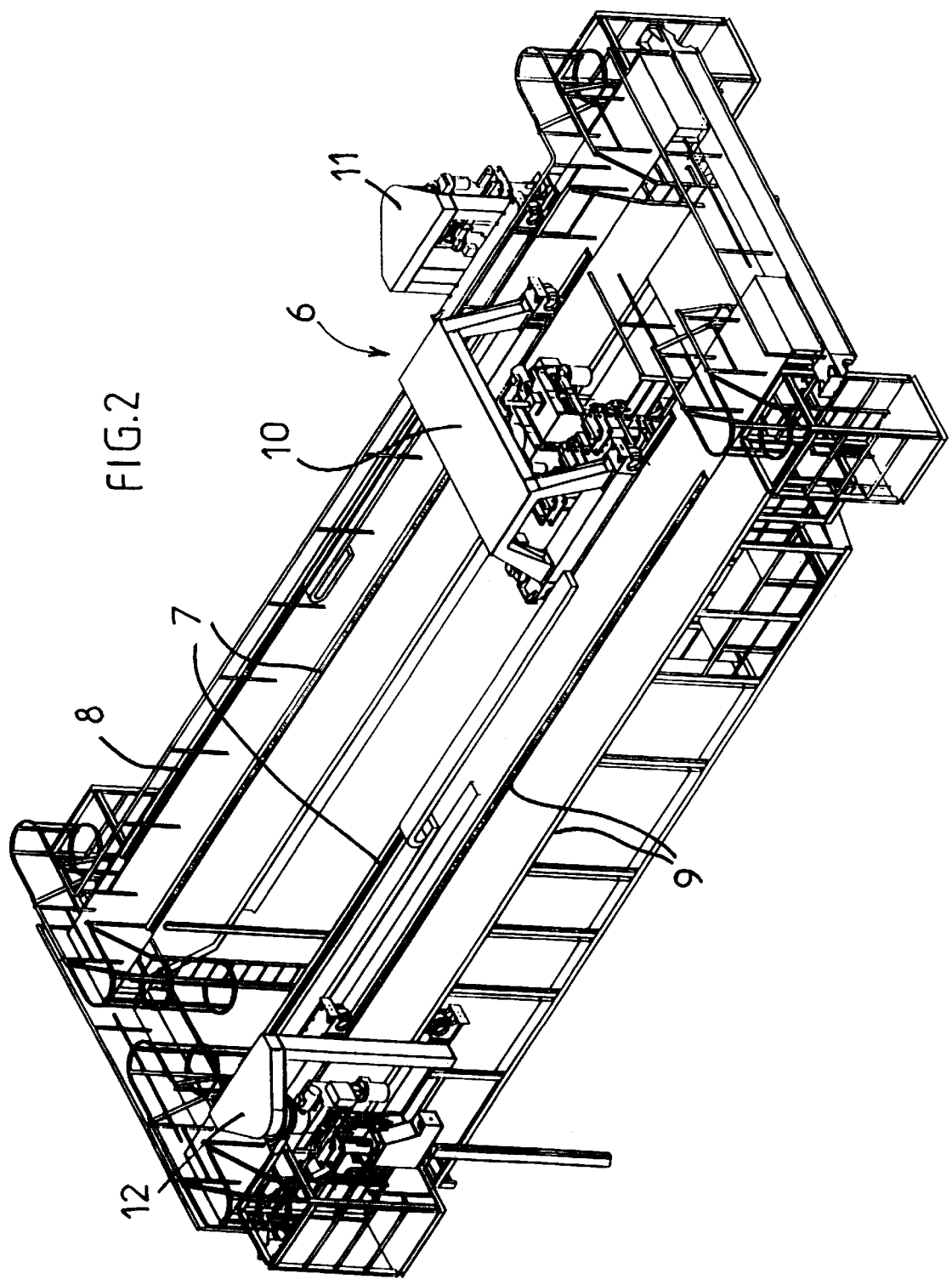

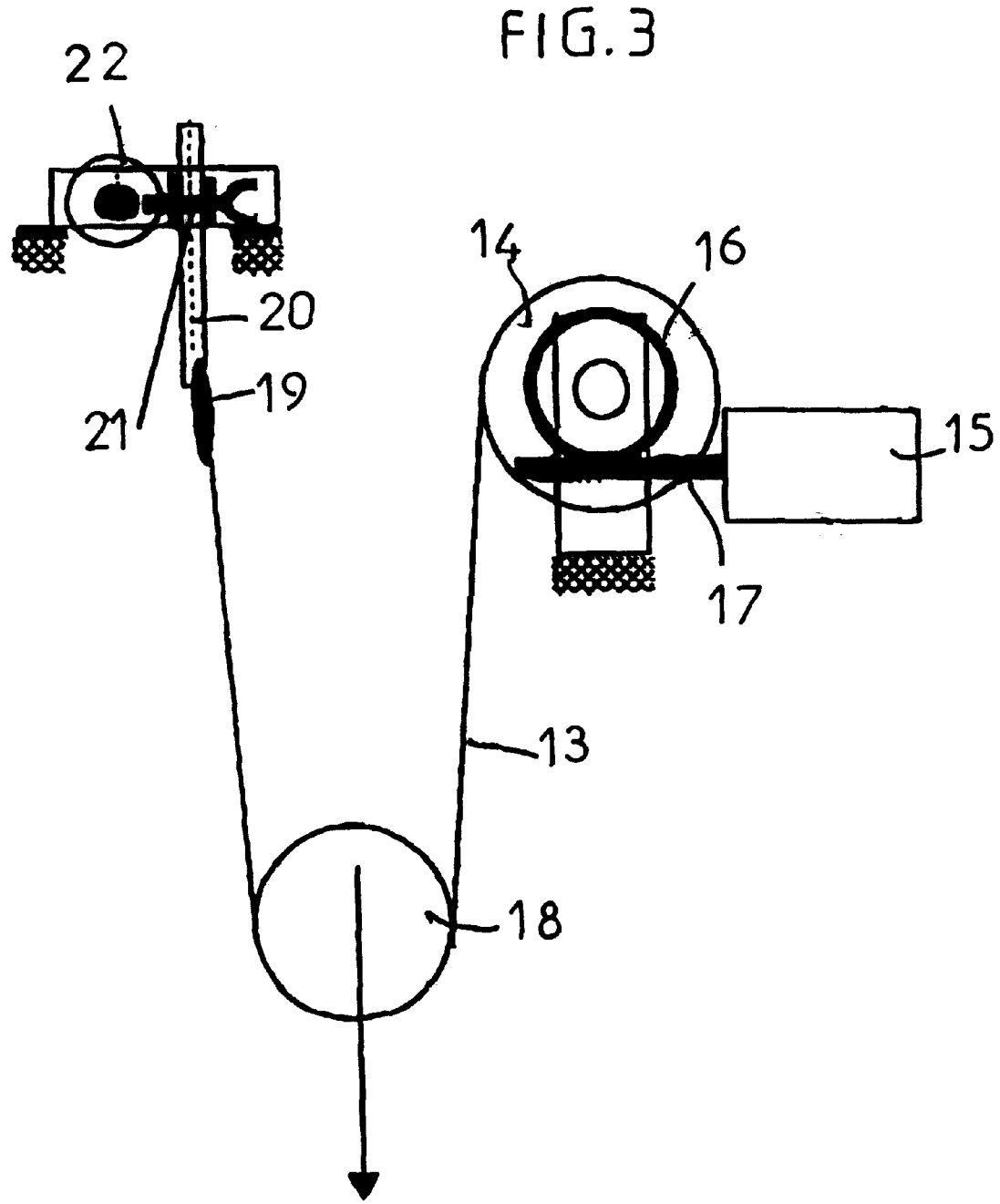

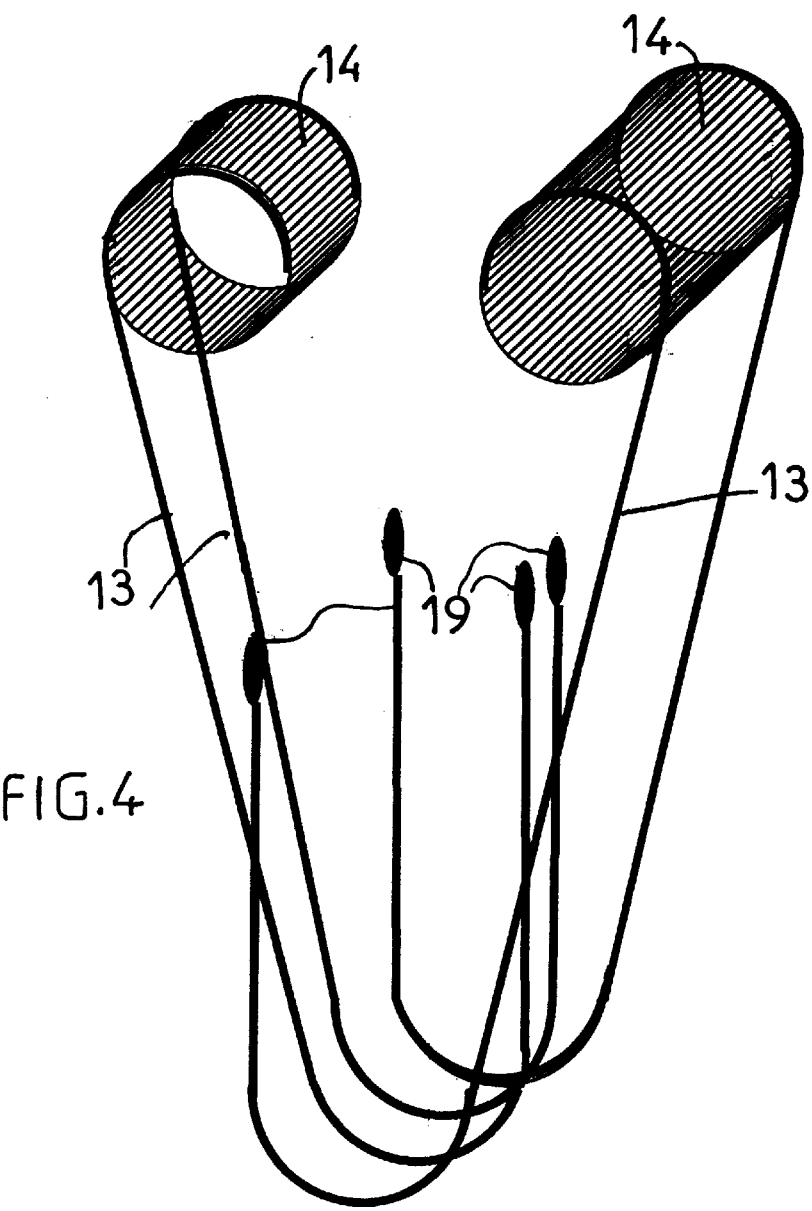
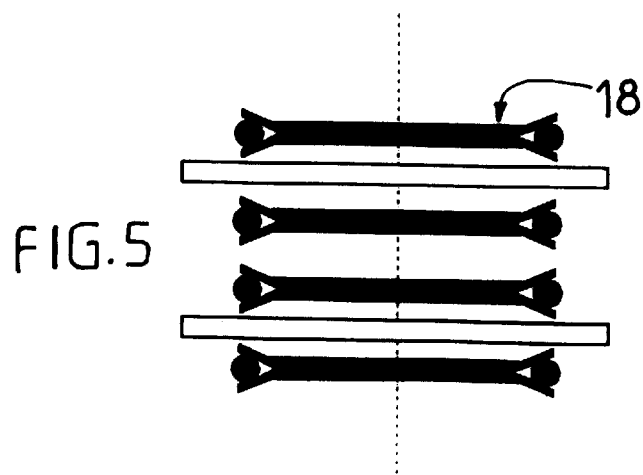

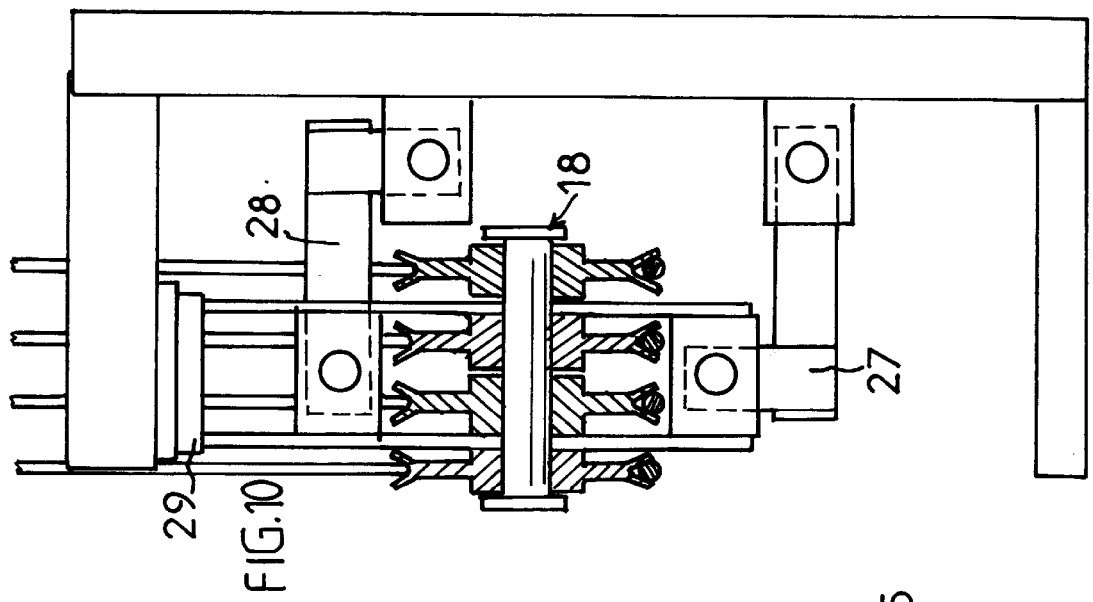
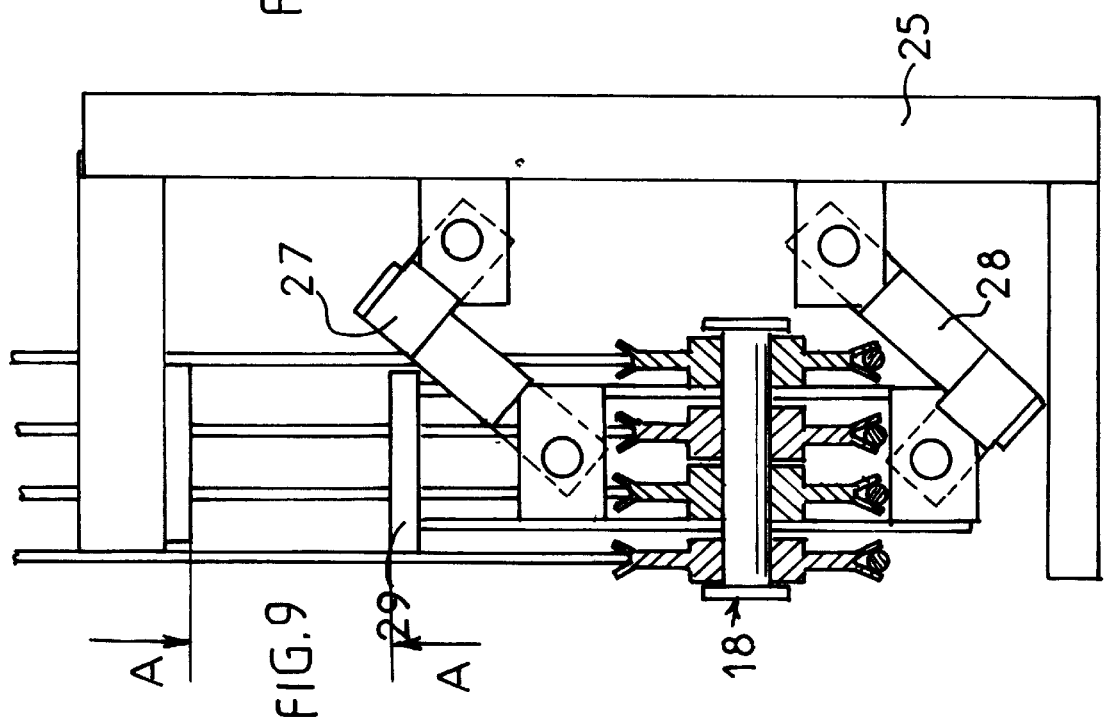

TOOL HOLDING DEVICE FOR THE EXTRACTION AND TRANSFER OF ANODES IN THE CENTER OF AN ALUMINUM FACTORY AND EQUIPMENT FOR OPERATING SUCH

BACKGROUND OF THE INVENTION

1. Field of the Invention

The present invention relates in general to the changing of spent anodes in aluminium production electrolysis tanks. It relates most specifically to a module which is able to allow the actual extraction of the spent anodes and to the installation employing such modules.

Aluminium is produced on an industrial scale by the now well-known process of dry electrolysis, that is to say a process involving electrolyzing alumina in a bath of molten cryolite according to the reaction:

This reaction, which is highly exothermic, therefore uses a molten bath containing a mixture of cryolite and alumina, the temperature of which is generally in excess of 800° C. and consumes a vast amount of electricity, which means that the plants operate continuously, so as to limit the energy losses that are inherent in re-start phases.

The various anodes, usually made of carbon, in each of the tanks need to be replaced regularly without stopping the electrolysis reaction to do so.

Because of the process employed, namely dry electrolysis, a hard crust of fluorinated cryolite alumina forms at the upper surface of the bath, this crust having the advantage of retaining heat within the bath and thus of creating an insulating envelope.

However, extracting the spent anodes from the bath first of all requires this crust to be broken, and experience has shown that the force needed to pull a spent anode out of said crust is seven to eight times greater than the mass of a fresh anode.

Furthermore, this force lasts for only a few centimeters of the distance, whereas the distance travelled for lifting the anode in each cycle is of the order of three to four meters, typically 3.50 m.

2. Description of the Related Art

To date, in existing plants, these operations have been performed using systems of hydraulic jacks which, to date, have only a limited size to allow them to fit into the volume available above the tanks.

However, regardless of the quality of the oil used in these hydraulic jacks, there is always a risk of fire given the high temperature of the molten bath, and there is a desire to escape from this prohibitive drawback.

Solutions hitherto proposed for avoiding the use of the hydraulic extraction system have run into a problem of size and of the civil engineering works of existing plants. Specifically, these solutions typically employ a cable system which takes up a greater amount of space which is incompatible with these plants or, requiring the production of new plants, have too significant an effect on the corresponding costs before they can be amortized.

BRIEF SUMMARY OF THE INVENTION

The object of the invention is therefore to propose an installation for changing spent anodes in a series of electrolysis tanks which avoids these drawbacks and in particular is compatible with the existing works and can avoid the risks inherent in the use of hydraulic devices. It relates firstly to a tool holder module, in particular, intended to take a tool to allow the spent anodes to be pulled out and transferred. This tool holder can also incorporate any type of tool and in particular a device capable of breaking the upper crust formed at the surface of the bath, but also a shovel or the like, intended to collect the pieces of crust that result from this breakage.

The tool holder module intended to be used in a lifting installation is characterized in that it is equipped with two independently motorized lifting members:

a first member, which consists of a set of cable(s) and electrically motorized drum(s) returned at a sheaving system, intended to displace a load at relatively high speed and over a relatively large distance;

a second member, one of the constituent elements of which is secured to the end of the cable or cables of said first member after return at the sheaving system and is intended, in cooperation with this system, to displace a heavier load vertically at a lower speed and over a limited distance.

The invention therefore consists, initially, in differentiating between two movements, namely a movement requiring an intense force over a short distance at a low speed, and a movement requiring a much lower force over a much longer distance, at a speed which is also far higher.

Principally, this module is most specifically suited to pulling out and transferring spent anodes. In fact, the second member is intended to allow the use of an intense pulling force needed and sufficient to allow the actual pulling of the spent anode out of the electrolysis bath whereas the first member, once said anode has actually been pulled out, displaces this anode outside of the tank.

According to one advantageous feature of the invention, the first member consists of a lifting system using cable(s), bearing one or more cables wrapped over one or more drums moved by an electric motor, and which are equipped with a sheaving system in the region of which a tool, for example for grasping the anode, for breaking the upper crust of the electrolysis bath, or alternatively a tool which acts as a shovel for collecting the pieces which come from said layer is attached.

In parallel, said second member consists of a mechanical or eletro-mechanical jack, to the end of which the cable or cables of said first member is/are attached.

In other words, the invention consists in producing a system for lifting a load, which system is equipped with a fixed point, it being possible for said fixed point to be made to move over a limited distance through the use of said second member, that is to say, in this particular instance, a mechanical or eletro-mechanical jack.

Advantageously, the module has slack in the cable, so as to limit the load applied by the tool with which said module is equipped, on an obstacle, and especially the bottom of the electrolysis tank. Furthermore, this slack in the cable makes it possible to keep the turns of cable perfectly wrapped around the drum or drums, and is also designed not to apply forces to the setdown plane, as specified in greater detail later.

According to another feature of the invention, the tool holder module comprises a semi-rigid vertical guide post secured to the chassis of said module, and along which an actual tool holder carriage slides. Since this is the case, the amplitude of the lateral travel of the sheaving system is limited, particularly near the maximum potential travel allowed by the length of the cables.

The invention also relates to the installation for changing spent anodes in electrolysis tanks for producing aluminium.

This installation comprises a travelling crane which can move over said tanks and on which there moves, in a direction perpendicular to the translational movement of the crane, at least one carriage equipped with a tool holder module intended to extract and transfer the spent anodes out of the tanks and to bring fresh anodes up to said tanks.

This installation is characterized in that it further comprises two more carriages, also capable of moving on the travelling crane in a direction perpendicular to the direction of displacement of the crane:

respectively a first carriage comprising a tool intended to break the surface crust created at the upper surface of the electrolysis bath of each of the tanks;

a second carriage comprising a tool equipped with shovel intended to allow all or some of the pieces resulting from breaking said crust to be collected; it being possible for the three carriages to move independently of one another.

The way in which the invention may be embodied and the advantages which stem from it will emerge better from the exemplary embodiment which follows, given by way of non-limiting indication with support from the appended figures.

BRIEF DESCRIPTION OF THE DRAWINGS

FIG. 1 is a diagrammatic depiction in perspective of part of a works for producing aluminium, showing a series of electrolysis tanks.

FIG. 2 is a diagrammatic depiction in perspective of the installation in accordance with the invention, in particular showing the travelling crane equipped with three distinct carriages.

FIG. 3 is a diagrammatic depiction relating to the principle of operation of the tool holder modules in accordance with the invention, of which FIG. 4 is a depiction of an example of a cabling system, and FIG. 5 a view on FIG. 4 from above.

FIGS. 9 and 10 are diagrammatic depictions of the way in which the slack in the cable used at said module in accordance with the invention operates.

DETAILED DESCRIPTION OF THE INVENTION

Figure 8:
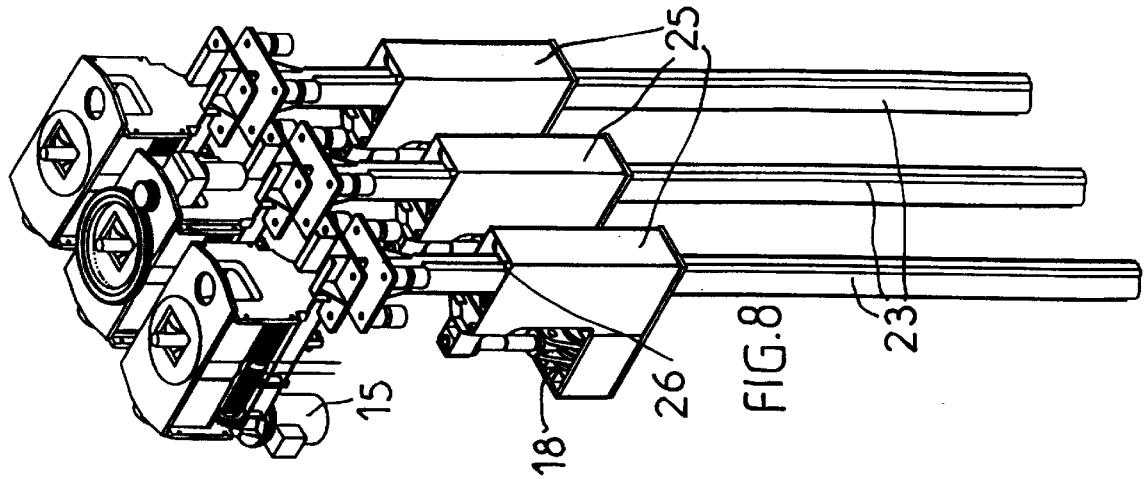
FIGS. 6, 7 and 8 are respectively diagrammatic depictions in perspective of the tool holder module in accordance with the invention, respectively alone and associated with two modules of the same type, in two different views.

FIG. 1 depicts a diagrammatic view of a series of electrolysis tanks (1) for producing aluminium according to the so-called dry electrolysis process, these tanks being installed in a works liable to contain several series of such tanks.

As can be seen, the plant comprises a number of tanks (1), essentially identical to each other, each of the tanks having a cover (2) for accessing the inside of the tank, and in particular the actual molten electrolysis bath, capable of thus yielding access, particularly to the carbon anodes (3).

As fluorin-containing gases, as well as carbon monoxide and dioxide which are generated by the electrolysis reaction are given off, each of the tanks is closed and fitted with a device for collecting gaseous effluent, in the form of pipes (4), said effluent generally being reprocessed to avoid discharging it as it is into the atmosphere.

The building containing this series of tanks is equipped with a runway (5) along which a travelling crane (6) can travel, this crane being depicted in greater detail in FIG. 2.

This travelling crane comprises, according to the invention, three independent sets of runways (7), (8), and (9), running at right angles to the runway (5), and along which carriages:

(10) supporting modules for bringing fresh anodes and removing the spent anodes, moving along the runway (7);

(11) supporting a tool for breaking the upper crust of the electrolysis baths, moving along the runway (8);

(12) supporting a tool, typically a shovel, for collecting all or some of the pieces resulting from breaking the crust, and moving along the runway (9), respectively, can travel.

Of course, each of these carriages has its own directional drive device, in particular using electric motors.

Furthermore, as can be clearly seen in FIG. 2, the two outermost carriages respectively carrying the crust-breaking tools and the shovel, are each equipped with two runways, respectively an upper one and a lower one, and therefore with complementary cooperation members, particularly rollers, allowing them to move uniformly and with guidance on the crane.

This installation proves particularly easy to operate: when a series of spent anodes needs to be changed, an operator, present at tank (1) level, opens the corresponding cover (2) and another operator starts to move the carriage (11) equipped with the member for breaking the upper crust at the appropriate point. To do this, the travelling crane (6) is itself moved to allow the carriage (11) to be positioned vertically over the area and tank concerned.

The carriage (12), equipped with the module that carries the shovel, is then brought in turn vertically above said tank by moving the travelling crane (6) and said carriage so as to allow the shovel to enter the tank in order to collect the pieces that result from breaking the crust. These pieces are removed to an appropriate area.

Finally, the carriage (10) for changing anodes is in turn brought vertically over the tank, and in particular brought to the anode-change point, and an operator begins to pull out the anodes concerned and remove them, also to a defined storage area, and to install the new anodes.

The tool holder modules employed in this installation will now be described in greater detail in connection with FIGS. 3 to 10.

According to a fundamental feature of the invention, each of the tool holder modules, and in particular the anode change modules, comprises two independent activation systems. They first of all comprise a system of cables (13) wrapped onto one or two drums (14), the latter being rotated by means of an electric motor (15) via a worm (17) and wheel (16) reduction gear set, each wheel (16) being secured to and coaxial with one of the drums (14) and cooperating with the worm (17) which is collinear with the drive shaft of the motor (15). These drums are positioned in the region of the upper chassis of each of the modules.

The cable or cables (13) is/are wrapped over two pulleys which constitute a sheaving system (18) and ascend towards a fixed point (19).

The load, and in particular the tool holder in question, is attached in the region of the sheaving system by any appropriate means, itself secured to a carriage (25) as described in greater detail later.

According to the invention, the fixed point (19) is itself secured to the end of the screw (20) of a mechanical jack (21), moved by an electric motor (22).

Thus, this double lifting system makes it possible to employ conventional lifting to shift the anodes over relatively long distances at a relatively high speed for a reduced load, and lifting with pulling out, capable of developing a strong force over a reduced distance at a limited speed.

Through its hauling capability, this device on the one hand is able to develop the force needed to pull out the spent anode which is to be replaced, but on the other hand, given the low corresponding speed, can make installing the fresh anode in the tank easier.

The members in the drive line, and in particular the wheels (16), the drums (14) and the cables (13) are dimensioned as a function of the intense force exerted by said second member, and to which they are subjected, given the stresses applied to them during the pulling-out phase.

Furthermore, choosing a worm and wheel (17, 16) reduction gear set for the high-speed motor that rotates the drums (14) makes it possible, by using the low indirect efficiency between the reduction gear set and the drum, to reduce the size of the brakes on the drive shaft of said motor (15) which are needed in the pulling-out phase, and therefore more generally makes it possible to reduce the overall size.

Advantageously, each of the tool holder modules is equipped with two drums (14) which are synchronized through the design of the reduction gear set, each taking two cables (13), so that the total number of cables is four, as depicted in particular in FIG. 4, for example. In this way it is possible to reduce the size of the pulleys, the drums and the reduction gear sets and, more generally, reduce the overall size of the device.

Figure 7:
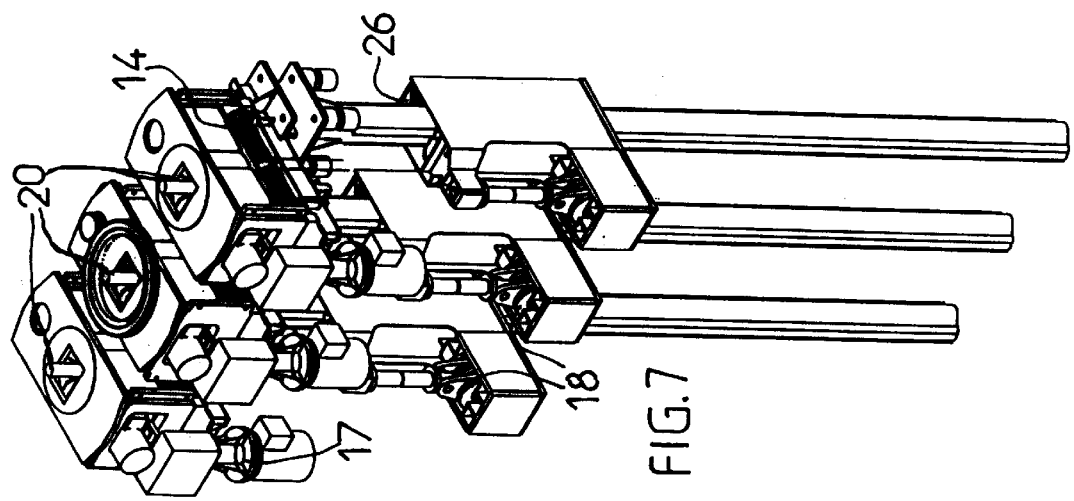

According to one advantageous feature of the invention, the tool holder modules changing the anodes are combined in threes, as depicted in FIGS. 7 and 8. This configuration is intended to allow three spent anodes to be changed simultaneously. Nonetheless, it is clearly understood that each of the modules can operate independently of each other, so that, not withstanding the use of a three-module system, just one or even just two of them may be activated for changing anodes.

The spacing between the three tool holder modules corresponds to the distance between centres of the anodes. This spacing may differ depending on the plant concerned, and is therefore adjustable. It is determined by link rods, the length of which corresponds to said distance between centres. This measure allows the system to be adapted to suit any type of plant.

Figure 6:
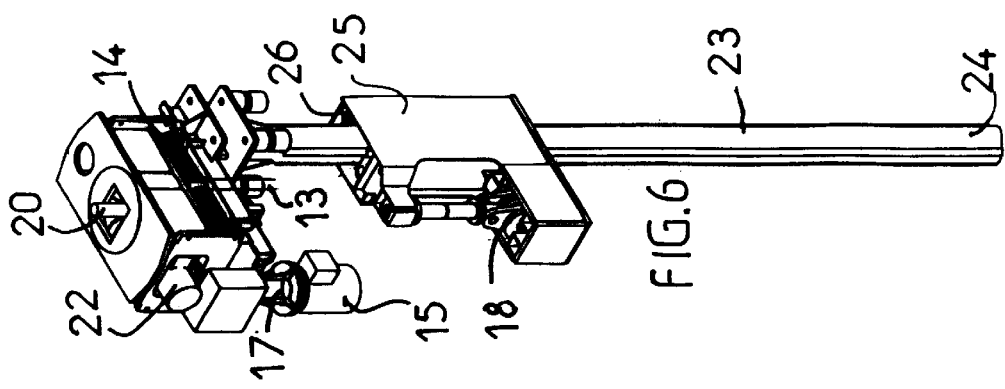

As may be seen in FIGS. 6 to 8, each tool holder module is associated with a vertical guide post (23), secured in the region of the upper chassis to the module via a preloaded device incorporating ball joints thus able to allow the lower part (24) of the post a certain degree of freedom. This post (23) is intended to provide guidance, particularly for a carriage (25) containing the sheaving system (18) and by extending the region from which the load is suspended, this carriage (25) being fitted with rollers (26) resting on each side of said post (23). This post is semi-rigid. The threshold for adjusting the preload is such that the risks of angular travel of said tool holder, particularly at the end of its travel, in the case of limited forces, and especially those inherent to the strong magnetic field which prevails in the plant, and to which the metallic elements that make up most of the elements involved in the construction of the module are subjected, are avoided.

According to another feature of the invention, each module has a system of slack in the cables, thus making it possible to limit the vertical travel of the tool when it encounters an obstacle, such as, for example, when the shovel touches the bottom of the tank. In this last instance, there is a desire to limit such a risk as far as possible, given the relative fragility of the tank. Furthermore, the slack in the cable allows the turns of cable on the drums (14) to be kept in perfect order.

This slack in the cable is described more particularly in connection with FIGS. 9 and 10. It is obtained by securing, in a non-fixed way, the sheaving system (18) to the carriage (25) that moves the tool holder along the post (23) by means of a set of two link rods (27, 28) which can move as a deformable parallelogram and are articulated respectively to the frame (29) in the region of which the sheaving system is mounted and to said carriage (25), the movement being between two extreme positions corresponding to the travel needed to take up the slack in the cable, which travel is depicted by the double arrow A in FIG. 9.

Thus, FIG. 9 depicts the carriage (25) resting on a nearby object or obstacle, the frame (29) no longer being in contact with said carriage (25). A sensor (not depicted) positioned between the carriage (25) and the frame (29) will have given the command to stop the lifting motor while a downwards movement was in progress. The maximum stopping distance of the mobile sheaving system is depicted by the double arrow A.

FIG. 10 depicts the carriage (25) suspended without contact with the surroundings, the frame (29) which carries the sheaving pulleys being in contact with the carriage (25).

Advantageously, a spring may be fitted between the upper face of the frame (29) and the carriage (25) so as to reduce the apparent weight of said carriage on a nearby object, this scenario safeguarding the electrolysis tank and its surroundings.

The tool holder module in accordance with the invention is dimensioned to tolerate forces on the charge of close to 10 tonnes for speeds of the order of one millimeter per second. By contrast, for speeds of the order of 15 meters per minute and far longer distances, the force during movement is of the order of 2 tonnes.

The use of such modules, activated electrically, has proved to be entirely adequate for existing plants that produce aluminium by electrolysis insofar that in particular, because of the physical separation between the functions associated with different loads, it allows the reactions of the rollers on the runways of the existing buildings to be limited and therefore requires no extension of the civil engineering works while at the same time allowing the safety conditions to be improved significantly.

What is claimed is:

1. An apparatus for changing spent anodes in a works for producing aluminum by dry electrolysis comprising:
    a travelling crane, wherein said crane moves in a first direction over electrolysis tanks;
    a first carriage mounted on said travelling crane, wherein said first carriage moves on a first runway in a second direction perpendicular to the first direction, and wherein said first carriage comprises a tool holder module and a tool for extracting and transferring anodes; and
    a second carriage mounted on said travelling crane, wherein said second carriage moves on a second runway in said second direction, wherein said second carriage moves on said second runway independently of the movement of said first carriage on said first runway, and wherein said second carriage comprises a tool holder module and a tool for breaking an upper crust on an aluminum electrolysis bath into pieces.

2. The apparatus of claim 1, wherein said first carriage further comprises a plurality of tool holder modules mounted in parallel.

3. The apparatus of claim 2, wherein said tool holder modules can operate independently.

4. The apparatus of claim 2, wherein a spacing between said tool holder modules is adjustable.

5. The apparatus of claim 4, wherein the spacing between said tool holder modules corresponds to a distance between centers of anodes.

6. The apparatus of claim 5, wherein said spacing is determined by link rods.

7. The apparatus of claim 1, further comprising a third carriage mounted on said travelling crane, wherein said third carriage moves on a third runway in said second direction, wherein said third carriage moves on said third runway independently of the movement of said first carriage on said first runway and said second carriage on said second runway, and wherein said third carriage comprises a tool holder module and a tool for collecting pieces from breaking said upper crust.

8. A tool holder module for lifting gear, said module having a chassis, comprising:
   a first lifting member comprising:
      at least one drum; and
      an electrical motor coupled to said at least one drum, said motor having a motor drive shaft;
   a second lifting member comprising a mechanical or electro-mechanical jack;
   a sheaving system comprising two pulleys, wherein the gear is attached to the sheaving system; and
   one or more cables, said cables having at least one end, wherein said one or more cables are wrapped over said one or more drums, around said pulleys, and are fixed to said jack by said at least one end,
   whereby said gear may be lifted by either said first lifting member or said second lifting member.

9. The tool holder module of claim 8, wherein said first lifting member lifts said gear at higher speed and with less force than said second lifting member.

10. The tool holder module of claim 8, wherein said electrical motor is coupled to said at least one drum via a worm and wheel reduction gear set.

11. The tool holder module of claim 10, wherein the wheel of said worm and wheel reduction gear set is secured to and coaxial with said at least drum.

12. The tool holder module of claim 10, wherein the worm of the worm and wheel reduction gear set is collinear with the motor drive shaft.

13. The tool holder module according to claim 8, wherein there is slack in said one or more cables.

14. The tool holder module according to claim 8, further comprising a semi-rigid vertical guide post, wherein said guide post is secured to the chassis of said tool holder module.

15. The tool holder module according to claim 14, further comprising a preloading device, wherein said preloading device secures said guide post to the chassis of said tool holder module, and wherein said preloading device allows the lower part of said guide post freedom of movement.

* * * * *

UNITED STATES PATENT AND TRADEMARK OFFICE
CERTIFICATE OF CORRECTION

PATENT NO. : 6,153,066
DATED : November 28, 2000
INVENTOR(S) : Gerard Piron

Page 1 of 1

It is certified that error appears in the above-identified patent and that said Letters Patent is hereby corrected as shown below:

Additions of assignees -- REEL SA -- and -- ASMI -- to the cover of the Letters Patent.

Signed and Sealed this

Thirty-first Day of July, 2001

*Attest:*

*Nicholas P. Godici*

*Attesting Officer*

NICHOLAS P. GODICI
*Acting Director of the United States Patent and Trademark Office*